United States Patent
Leyshon et al.

(10) Patent No.: US 7,816,572 B2
(45) Date of Patent: Oct. 19, 2010

(54) PROPYLENE AND ISOPRENE PRODUCTION

(75) Inventors: David W. Leyshon, West Chester, PA (US); Thomas S. Zak, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 612 days.

(21) Appl. No.: 11/890,728

(22) Filed: Aug. 7, 2007

(65) Prior Publication Data

US 2009/0043144 A1 Feb. 12, 2009

(51) Int. Cl.
 *C07C 5/00* (2006.01)
(52) U.S. Cl. .................. 585/324; 585/644; 585/332; 585/654; 585/656
(58) Field of Classification Search .............. None
 See application file for complete search history.

(56) References Cited

U.S. PATENT DOCUMENTS

| | | | |
|---|---|---|---|
| 3,326,866 A | 6/1967 | Haag | 260/79.3 |
| 3,531,545 A | 9/1970 | Garner et al. | 260/683.2 |
| 3,541,172 A | 11/1970 | Stowe et al. | 260/669 |
| 3,621,073 A | 11/1971 | McGrath et al. | 260/683 D |
| 4,085,158 A * | 4/1978 | Dixon et al. | 585/326 |
| 4,164,519 A | 8/1979 | Bertus | 585/622 |
| 4,242,530 A | 12/1980 | Smith, Jr. | 585/510 |
| 4,443,559 A | 4/1984 | Smith, Jr. | 502/527 |
| 4,515,661 A | 5/1985 | Ogura et al. | 203/60 |
| 4,536,373 A | 8/1985 | Jones, Jr. | 422/211 |
| 4,731,229 A | 3/1988 | Sperandio | 422/188 |
| 4,774,364 A | 9/1988 | Chou | 568/697 |
| 4,847,430 A | 7/1989 | Quang et al. | 568/697 |
| 4,935,577 A | 6/1990 | Huss, Jr. et al. | 585/726 |
| 4,992,612 A | 2/1991 | Suzukamo et al. | 585/664 |
| 4,992,613 A | 2/1991 | Brownscombe | 585/666 |
| 5,073,236 A | 12/1991 | Gelbein et al. | 203/29 |
| 5,120,894 A | 6/1992 | McCauley | 585/664 |
| 5,153,165 A | 10/1992 | Lowery et al. | 502/341 |
| 5,196,612 A | 3/1993 | Ward | 568/697 |
| 5,288,370 A | 2/1994 | Asselineau et al. | 203/51 |
| 5,300,718 A | 4/1994 | McCaulley | 585/324 |
| 5,348,710 A | 9/1994 | Johnson et al. | 422/211 |
| 5,395,981 A | 3/1995 | Marker | 568/697 |
| 5,431,890 A | 7/1995 | Crossland et al. | 422/211 |
| 5,510,089 A | 4/1996 | Jones | 422/189 |
| 5,744,645 A | 4/1998 | Marker et al. | 565/695 |

(Continued)

OTHER PUBLICATIONS

*Chem. Eng. Prog.* (Mar. 1992) 43.

(Continued)

*Primary Examiner*—Tam M Nguyen
(74) *Attorney, Agent, or Firm*—Yuanzhang Han

(57) ABSTRACT

A process for producing propylene and isoprene from a feed stream comprising 1-butene and isobutene is disclosed. The feed stream is reacted in a catalytic distillation reactor containing an olefin isomerization catalyst to produce an overhead stream comprising 2-butene and isobutene and a bottoms stream comprising 2-butene. The overhead stream is reacted in the presence of a metathesis catalyst to produce propylene and isoamylenes. Isoprene is produced by dehydrogenation of isoamylenes.

20 Claims, 1 Drawing Sheet

U.S. PATENT DOCUMENTS

| | | |
|---|---|---|
| 6,586,649 B1 | 7/2003 | Botha et al. .................. 585/646 |
| 6,852,901 B2 | 2/2005 | Hasenberg et al. .......... 585/664 |
| 2003/0004385 A1 | 1/2003 | Gartside et al. ............. 585/664 |
| 2003/0204124 A1* | 10/2003 | Podrebarac ................ 585/646 |
| 2004/0192994 A1 | 9/2004 | Bridges et al. .............. 585/664 |
| 2004/0249229 A1 | 12/2004 | Gee et al. ................... 585/664 |
| 2005/0080309 A1 | 4/2005 | Cano et al. .................. 585/664 |
| 2005/0154246 A1 | 7/2005 | Adrian et al. ............... 585/862 |
| 2006/0052652 A1 | 3/2006 | Stark et al. .................. 585/275 |
| 2006/0084831 A1 | 4/2006 | Zhang ........................ 585/670 |

OTHER PUBLICATIONS

*Appl. Ind. Catal.* 3 (1984) 215.

N. Calamur et al., "Butylenes" in *Kirk-Othmer Encyclopedia of Chemical Technology*, Online Edition (2007).

A. J. deRosset et al., *Prepr.-Am.Chem.Soc., Div. Pet. Chem.* 23(2) (1978) 766.

*Hydrocarbon Process., Int. Ed.* (May 1979) 112.

* cited by examiner

PROPYLENE AND ISOPRENE PRODUCTION

FIELD OF THE INVENTION

The invention relates to a process for producing propylene and isoprene from a feed stream comprising 1-butene and isobutene.

BACKGROUND OF THE INVENTION

Steam cracking of hydrocarbons is widely used to produce olefins such as ethylene, propylene, butenes (1-butene, cis- and trans-2-butene, isobutene), butadiene, and aromatics such as benzene, toluene, and xylene. In an olefin plant, a hydrocarbon feedstock such as naphtha, gas oil, or other fractions of whole crude oil is mixed with steam. This mixture, after preheating, is subjected to severe thermal cracking at elevated temperatures (1500° F. to 1600° F.) in a pyrolysis furnace. The cracked effluent from the pyrolysis furnace contains gaseous hydrocarbons of great variety (from 1 to 35 carbon atoms per molecule). This effluent contains hydrocarbons that are aliphatic, aromatic, saturated, and unsaturated, and may contain significant amounts of molecular hydrogen. The effluent is then further separated into various individual product streams such as hydrogen, ethylene, propylene, mixed hydrocarbons having four or five carbon atoms per molecule (crude $C_4$'s and $C_5$'s), and pyrolysis gasoline.

Crude $C_4$'s can contain varying amounts of n-butane, isobutane, 1-butene, 2-butene (cis- and/or trans-), isobutene, acetylenes (ethyl acetylene and vinyl acetylene), and butadiene. As used herein, "2-butene" includes cis-2-butene, trans-2-butene, or a mixture of both. See N. Calamur, et al., "Butylenes," in *Kirk-Othmer Encyclopedia of Chemical Technology*, online edition, 2007.

Crude $C_4$'s are typically subjected to butadiene extraction or butadiene selective hydrogenation to remove most, if not essentially all, of the butadiene and acetylenes present. Thereafter the $C_4$ raffinate (called raffinate-1) is subjected to a chemical reaction (e.g., etherification, hydration, dimerization) wherein the isobutene is converted to other compounds (e.g., methyl tertiary butyl ether, tertiary butyl alcohol, diisobutene) (see, e.g., U.S. Pat. Nos. 6,586,649 and 4,242,530). The remaining $C_4$ stream containing mainly n-butane, isobutane, 1-butene, and 2-butene is called raffinate-2.

When the market demand for methyl tertiary butyl ether declines, the conversion of isobutene from raffinate-1 to methyl tertiary butyl ether may not be economical. It is desirable to produce other useful products from raffinate-1.

Methods for producing isoamylene and/or isoprene from $C_4$ streams are known. U.S. Pat. No. 3,621,073 teaches a method of converting butenes to isoamylene through a series of steps including purification, isomerization of 1-butene to 2-butene at a temperature below 0° C., and a metathesis reaction of 2-butene and isobutene to produce isoamylene. The disadvantage of the process is that the isomerization reaction, even at below 0° C. only partially converts 1-butene to 2-butene, thus complicating the down-stream purification and reaction steps.

U.S. Pat. No. 4,085,158 teaches a method of producing isoamylenes from butenes comprising steps of separating 1-butene from a mixed butenes stream to produce a mixture of 2-butene and isobutene by molecular sieves adsorption and desorption, metathesis of 2-butene and isobutene, and isomerization of 1-butene to 2-butene. This method suffers from the high operating cost of the adsorption step due to the limited capacity of the adsorbent.

SUMMARY OF THE INVENTION

The invention is a process for producing propylene and isoprene from a feed stream comprising 1-butene and isobutene. The feed stream is reacted in a catalytic distillation reactor containing an olefin isomerization catalyst to produce an overhead stream comprising 2-butene and isobutene and a bottoms stream comprising 2-butene. The overhead stream is reacted in the presence of a metathesis catalyst to produce propylene and isoamylenes. Isoprene is produced by dehydrogenation of isoamylenes. The invention provides a method of producing useful petrochemical intermediates from a raffinate-1 stream.

DETAILED DESCRIPTION OF THE INVENTION

Figure 1:
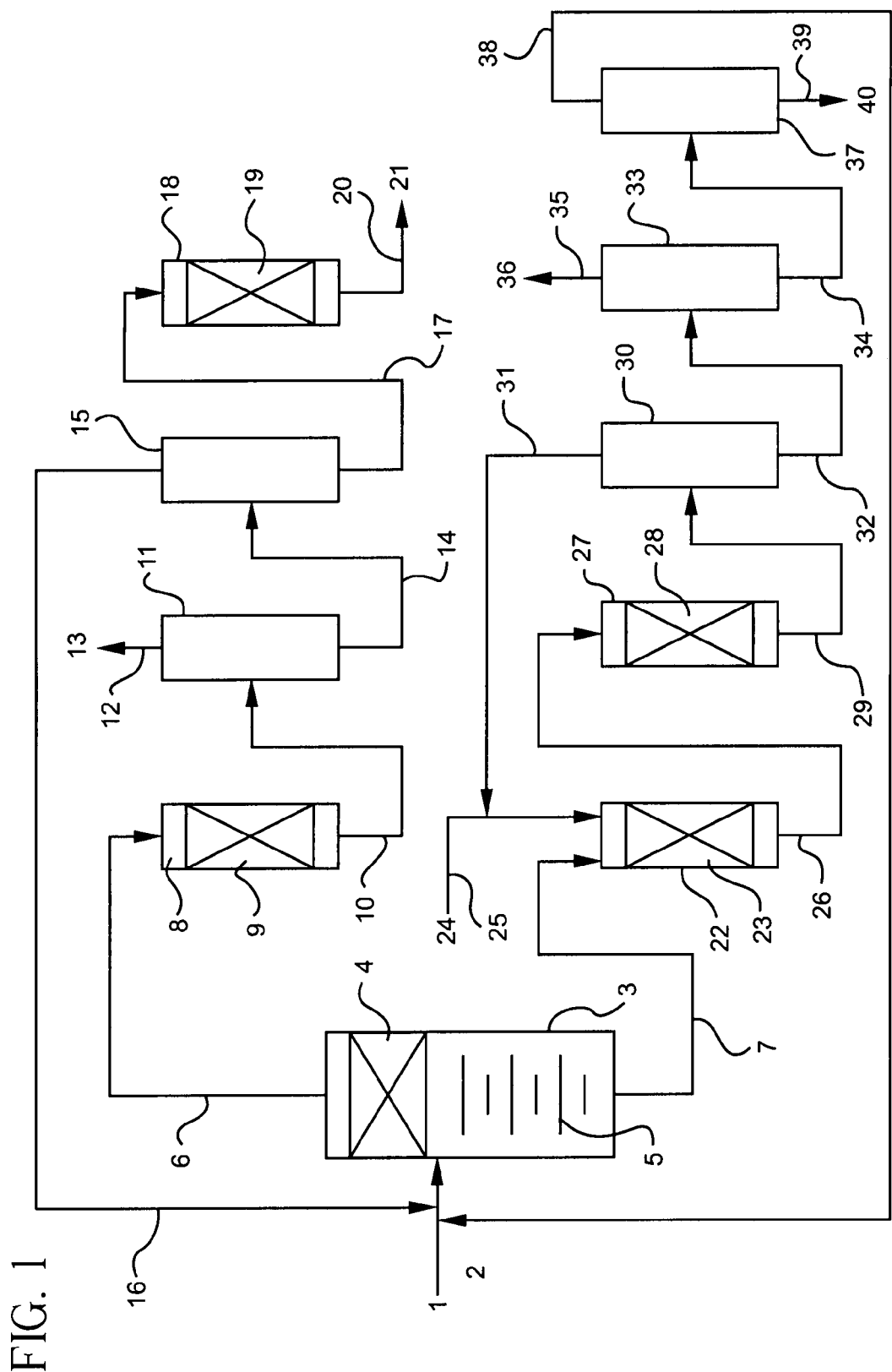
FIG. 1 is a schematic flow diagram of one embodiment of the invention.

The process comprises: (a) reacting a feed stream comprising 1-butene and isobutene in the presence of an isomerization catalyst to generate a first reaction mixture, and concurrently distilling the first reaction mixture to produce an overhead stream comprising 2-butene and isobutene and a bottoms stream comprising 2-butene; (b) reacting the overhead stream in the presence of a first metathesis catalyst to generate a second reaction mixture comprising isoamylenes, butenes, and propylene; (c) distilling the second reaction mixture to isolate isoamylenes; and (d) dehydrogenating the isoamylenes from step (c) to produce isoprene.

Any feed stream comprising 1-butene and isobutene may be used. The feed stream may comprise other components such as 2-butene. Preferably, the feed stream is primarily composed of 1-butene, 2-butene, and isobutene. For example, the amount of 1-butene, 2-butene, and isobutene combined in the feed stream is desirably at least 95 weight percent (wt. %), more desirably at least 99 wt. % of the total hydrocarbons in the feed stream.

One suitable feed stream is obtained from raffinate-1, which is a crude $C_4$ stream from refining or steam cracking processes. Raffinate-1 contains mostly 1-butene, 2-butene, isobutene, n-butane, and isobutane. Preferably, paraffins are removed from raffinate-1 by extractive distillation with a suitable extractive solvent (e.g., acetonitrile, dimethyl formamide, N-methylpyrrolidone, or N-formyl morpholine). See U.S. Pat. Nos. 4,515,661, 5,288,370, U.S. Pat. Appl. Pub. No. 2005/0154246. Such separation may also be performed by adsorption. See DeRosset, A. J., et al., *Prepr.-Am. Chem. Soc., Div. Pet. Chem.* (1978) 23(2) 766.

One suitable extractive distillation method for removing paraffins from a raffinate-2 is described in U.S. Pat. Appl. Pub. No. 2005/0154246. A similar method may be applied to remove paraffins from a raffinate-1 stream. Thus, a raffinate-1 stream containing 1-butene, 2-butene, isobutene, n-butane, and isobutane is subjected to an extractive distillation in an absorber. The raffinate-1 stream is fed as a gas or a liquid, preferably in gaseous form. An extractive solvent (e.g., N-methylpyrrolidone) is fed in liquid form above the point where the raffinate-1 stream is fed. Through the countercurrent contact between the raffinate-1 and the solvent, the raffinate-1 stream is separated into an overhead stream comprising the saturated components, i.e., the components for which the solvent has lower affinities; and a bottoms stream that comprises the solvent laden with components for which the extractive solvent has higher affinities. Preferably the raffinate-1 stream is fed at the lower region of the absorber. There are no restrictions regarding the internals which can be used in the column. It is possible to use trays, random packing or structured packing. The column advantageously has from 10 to 120, preferably from 50 to 100, theoretical stages. A small amount of solvent (preferably less than 1 wt. % of the total weight of the top stream) may be present in the top stream, which may be removed from the stream in a subsequent water wash step.

The pressure in the absorber is dependent on the temperature of the cooling medium in the condenser at the top of the column (well water, river water, seawater, refrigerant such as liquid propylene, liquid ammonia or brine). It is generally at a pressure of from 20 to 200 psig, frequently from 50 to 100 psig. The temperature in the column is, on the basis of the above-mentioned pressure values, set so as to give suitable thermodynamic conditions under which the extractive solvent becomes laden with butenes while the butanes in the feed stream remain in the gas phase. The temperature at the top of the column is typically in the range of from 90 to 140° F. The temperature at the bottom is typically in the range of from 150 to 250° F.

The bottoms stream from the absorber is separated in a stripper at a higher temperature and/or lower pressure compared to the absorber into an overhead stream comprising the butenes and small amount of other hydrocarbons and a bottoms stream comprising the solvent. Suitable temperatures for the stripper are in the range of from 90 to 300° F. The recovered solvent is recycled to the absorber.

The overhead stream of the stripper is a suitable feed stream for the invention. It is fed in a distillation column reactor containing an isomerization catalyst to form a first reaction mixture comprising 1-butene, 2-butene, and isobutene. In a distillation column reactor, reactants are converted to products over a solid catalyst and at the same time distillation of the reaction mixture occurs to separate the mixture into two or more fractions. Such a technique is called reactive distillation or catalytic distillation. Catalytic distillation is well known in the chemical and petrochemical industries (see, e.g., U.S. Pat. Nos. 4,935,577, 5,395,981, 5,196,612, 5,744,645, U.S. Pat. Appl. Pub. Nos. 2004/0192994, 2005/080309, and 2006/052652). Olefin isomerizations are known to be carried out in distillation column reactors (see, e.g., U.S. Pat. Appl. Pub. No. 2006/052652).

An isomerization catalyst is contained in the distillation column reactor. Olefin isomerization catalysts are well known in the art. Many isomerization catalysts can be used, including acidic catalysts, basic catalysts, and hydroisomerization catalysts. Suitable acidic catalysts include acidic ion-exchange resins such as sulfonated resins (see, e.g., U.S. Pat. No. 3,326,866), metal oxides (aluminas, zirconias, sulfated zirconias), mixed oxides (e.g., silica-aluminas, zirconia-silicas), acidic zeolites, acidic clays (see, e.g., U.S. Pat. Nos. 4,992,613 and 6,852,901; U.S. Pat. Appl. Pub. Nos. 2004/249229, 2006/084831).

The basic isomerization catalysts are preferably metal oxides such as magnesium oxide (magnesia), calcium oxide, barium oxide, and lithium oxide. Metal oxides supported on a carrier may be used. Suitable carriers include silicas, aluminas, titanias, silica/aluminas, and the like, and mixtures thereof (see, e.g., U.S. Pat. Nos. 5,153,165, 5,300,718, 5,120,894, 4,992,612, U.S. Pat. Appl. Pub. No. 2003/0004385). A particularly preferred basic isomerization catalyst is magnesium oxide. Suitable magnesium oxide has a surface area of at least 1 $m^2/g$, preferably at least 5 $m^2/g$. The magnesium oxide is preferably activated in a suitable manner, for example, by heating in a flowing stream of an oxygen-containing gas for about 0.1 to about 30 h at 250 to 800° C., preferably at 300 to 600° C. before use.

The isomerization may be catalyzed by a hydroisomerization catalyst in the presence of small amount of hydrogen. Hydroisomerization of olefins is well known (*Hydrocarbon Process., Int. Ed.* May 1979, 112). Suitable catalysts include supported noble metal catalysts (e.g., Pd or Pt supported on silicas or aluminas, see U.S. Pat. No. 3,531,545). The hydrogen to butenes molar ratio is typically in the range of 1:10 to 1:100. The hydroisomerization of the feed stream is particularly preferred if the feed stream contains small amount of butadiene or acetylenes. A hydroisomerization process not only converts 1-butene to 2-butene, it also converts butadiene or $C_4$-acetylenes to mono-olefins such as 1-butene and 2-butene.

In the distillation column reactor, the isomerization catalyst functions both as a catalyst and as distillation packings. In other words, packings in a column distillation reactor serve both a distillation function and a catalytic function.

The isomerization catalyst may be a powder or particulates. Particulate catalysts are preferred. The catalyst particles such as beads, granules, pellets, extrudates, tablets, agglomerates, honeycomb monolith, and the like are sufficiently large so as not to cause high pressure drops through the column.

Alternatively, the catalyst may be incorporated into the packings or other structures (see *Chem. Eng. Prog.* March 1992, 43). Preferred catalyst structures for use in the distillation column reactors comprises flexible, semi-rigid open mesh tubular material, such as stainless steel wire mesh, filled with a particulate catalyst. Other structures suitable for the present invention can be found in U.S. Pat. Nos. 4,242,530, 4,443,559, 4,536,373, 4,731,229, 4,774,364, 4,847,430, 5,073,236, 5,348,710, 5,431,890, and 5,510,089. For example, U.S. Pat. Nos. 4,242,530 and 4,443,559 disclose particulate catalysts in a plurality of pockets in a cloth belt or wire mesh tubular structures, which are supported in the distillation column reactor by open mesh knitted stainless steel wire by twisting the two together into a helix. Optionally, additional internal stages in the form of packings or trays are installed below the catalyst bed.

The distillation column reactor is typically equipped with an overhead cooler, condenser, a reflux pump, a reboiler, and standard control instrumentations.

The distillation column reactor contains a vapor phase and a liquid phase, as in any distillation. The success of the concurrent distillation and reaction approach lies in an understanding of the principles associated with distillation. First, because the reaction is occurring concurrently with distillation, the initial reaction products are removed from the reaction zone as quickly as possible. Second, because all the components are boiling, the reaction temperature is controlled by the boiling point of the mixture at the system pressure. The heat of reaction simply creates more boiling, but no increase in temperature. Third, the reaction has an increased driving force because the reaction products are removed and cannot contribute to a reverse reaction. As a result, a great deal of control over the rate of reaction and distribution of products can be achieved by regulating the system pressure.

The temperature in a distillation column reactor is determined by the boiling point of the liquid mixture present at a given pressure. The temperature in the lower portions of the column reflects the composition of the material in that part of the column, which is higher than the overhead; that is, at constant pressure a change in the temperature of the system indicates a change in the composition in the column. Temperature control in the reaction zone is thus effected by a change in pressure; by increasing the pressure, the temperature in the system is increased, and vice versa. The pressure of the distillation column reactor is low enough to allow nearly all isobutene and a portion of 2-butene to exit the partial condenser as vapor, but high enough so that at least a portion of 1-butene is converted to 2-butene in the catalyst bed. As a result, the overhead stream coming out of the catalytic distillation reactor contains primarily 2-butene and isobutene; and the bottoms stream contains primarily 2-butene. Generally at least 60 mole %, preferably at least 80 mole % of 1-butene present in the feed stream is converted to 2-butene in the distillation column reactor. Suitable temperatures to operate this column are in the range of 100 to 300° F.; and suitable pressures range from 50 to 250 psig.

The overhead stream of the distillation column reactor is reacted in the presence of a first metathesis catalyst to generate a second reaction mixture comprising isoamylenes, butenes, and propylene. Isoamylenes include 2-methyl-2-butene, 2-methyl-1-butene, and 3-methyl-1-butene. Metathesis catalysts are well known in the art (see, e.g., *Appl. Ind. Catal.* 3 (1984) 215). Typically, a metathesis catalyst comprises a transition metal oxide. Suitable transition metal oxides include oxides of cobalt, molybdenum, rhenium, tungsten, and mixtures thereof. Conveniently, the transition metal oxide is supported on a carrier. Suitable carriers include silicas, aluminas, titanias, zirconias, zeolites, clays, and mixtures thereof. Silicas and aluminas are preferred. The transition metal oxide may be supported on a carrier in any convenient fashion, in particular by adsorption, ion-exchange, impregnation, or sublimation. The transition metal oxide constituent of the catalyst may amount to 1 to 30 wt. % of the total catalyst, preferably 5 to 20 wt. %. Tungsten oxide-on-silica is a preferred catalyst. More preferably, a catalyst comprising tungsten oxide, silica, and magnesium oxide is used. For example, a mixture of magnesium oxide and tungsten oxide-on-silica may be used.

Particulate metathesis catalysts are preferred. The catalyst particles such as beads, granules, pellets, extrudates, tablets, agglomerates, honeycomb monolith, and the like must be sufficiently large so as not to cause high pressure drops through the bed.

The second reaction mixture is distilled into propylene, a butenes stream, and an isoamylenes stream. The separation may be performed in a single distillation column. Alternatively, two distillation columns may be used (see Example).

The isoamylenes stream is dehydrogenated to produce isoprene. The dehydrogenation reaction may be performed in a fixed-bed or a fluidized-bed reactor. Oxidative dehydrogenation catalysts are known in the art (see, e.g., U.S. Pat. Nos. 3,541,172 and 4,164,519). Teachings of suitable oxidative dehydrogenation catalysts and their preparation methods disclosed in above documents are incorporated herein by reference.

The bottoms stream of the distillation column reactor comprises mostly 2-butene, which may be used as a petrochemical intermediate for other chemical processes. Alternatively, the bottoms stream is further processed into other products. It may be reacted with ethylene in the presence of a second metathesis catalyst to produce a third reaction mixture comprising ethylene, propylene, 1-butene, 2-butene, and $C_5$ and higher olefins. Suitable metathesis catalysts described in the previous section may be applied in the present step. Typically the metathesis is conducted in a fixed-bed reactor at a temperature of 500 to 850° F. and under a pressure of from 200 to 600 psig.

The third reaction mixture is distilled into ethylene, propylene, a butenes stream, and a heavy stream comprising $C_5$ and higher olefins. The separation may be achieved with one or more distillation columns. For example in a three-column-separation scheme (as shown in the Example), ethylene is separated as an overhead stream from a first column and is recycled to the metathesis reaction of the bottoms stream of the column distillation reactor and ethylene. In the Example, the bottoms stream from the first column 30 is separated in a second column 33 into an overhead stream containing propylene, and a bottoms stream containing butenes and $C_5$ and higher olefins, see FIG. 1. The bottoms stream of the second column is separated in a final column 37 into a butenes stream and a $C_5$ and higher olefins stream. The butenes stream is preferably recycled to step (a).

Sometimes it is desirable to treat a feed to a metathesis reaction with an adsorption bed to remove impurities to extend the catalyst life (see U.S. Pat. No. 5,120,894). Either the overhead stream from step (a) or the combined stream containing ethylene and the bottoms stream from step (a) may be treated by such an adsorption bed. Olefin metathesis processes in general require the substantial absence of impurities that can deactivate the catalyst. Some of these impurities are, e.g., water, alcohols, aldehydes, ketones, ethers, carboxylic acids, esters, sulfur-containing compounds, and nitrogen-containing compounds. Many adsorbents may be used such as silicas, aluminas, zeolites, clays, and the like. Aluminas are particularly preferred. The contact with the adsorbent can be either in vapor or liquid phase, but preferably in liquid phase. Adsorption is typically carried out at a pressure of 100 to 600 psig, a temperature in the range of 60 to 200° F., and a weight hourly space velocity in the range of from 0.5 to 10 $h^{-1}$.

EXAMPLE

Paraffins are removed from a $C_4$ raffinate-1 stream by extractive distillation with acetonitrile as an extractive solvent. The remaining $C_4$'s are used as feed to a process shown in FIG. 1. Table 1 lists the composition of the feed (stream 2). Stream 2 is mixed with stream 16 and stream 38 (described below) and sent to the catalytic distillation reactor 3. A small amount of hydrogen (130 lb/h, not included in Table 1) is fed to reactor 3. Reactor 3 contains a Pd/alumina (0.3 wt. % Pd) catalyst in its upper portion for isomerizing 1-butene to 2-butene. The lower portion of the reactor strips lighter components, such as isobutene and 1-butene out of the bottoms product, which is mainly 2-butene. Primarily isobutene and 2-butene, with small amount of 1-butene, are removed from the top of the reactor as stream 6. Stream 6 is fed to a metathesis reactor 8 containing magnesium oxide and 7 wt. % $WO_3$-on-silica in bed 9. In reactor 8, isobutene is reacted with linear butenes (mostly 2-butene) to form stream 10 containing isoamylenes, propylene, and ethylene. Stream 10 is fed to a distillation tower 11 to separate ethylene and propylene. Tower 11 contains 50 ideal stages. The pressure is 400 psig in the overhead and 410 psig in the bottoms. The overhead temperature is at 119° F. and the bottoms temperature is 320° F. The reflux ratio is 4:1 by weight. The bottoms from tower 11 is fed to tower 15. The purpose of tower 15 is to recover unreacted $C_4$'s so that they can be recycled to the front end of the process. The composition of the recycle stream 16 is shown in Table 1. Tower 15, which contains 30 ideal stages, is operated at an overhead pressure of 100 psig and an overhead temperature of 134° F. The bottom temperature is 244° F. The reflux ratio is 3:1 by weight. The bottoms of tower 15 is heated to 1130° F. and fed to dehydrogenation reactor 19, where the isoamylenes are converted to isoprene. The gas hourly space velocity for the reaction is 152 h$^{-1}$. The catalyst used is a strontium nickel phosphate catalyst described in U.S. Pat. No. 3,541,172. For every mole of hydrocarbons fed, 20 moles of steam is fed to the reactor.

Stream 7, which is the bottoms from tower 3, contains mostly 2-butene. Stream 7 is mixed with ethylene and treated with an alumina bed 23 to remove trace impurities. The resulting stream 26 is fed to reactor 27, where it is reacted in the presence of a mixture of magnesium oxide and a 7 wt. % WO$_3$-on-silica at 650° F. and 450 psig to form propylene. Stream 29 is distilled in tower 30 to recover unreacted ethylene (stream 31), which is recycled. Tower 30 is operated at an overhead pressure of 400 psig and at a bottoms pressure of 410 psig. The overhead temperature is 2° F. and the bottoms temperature is 182° F. Tower 30 contains 100 ideal stages and is operated with a 4:1 reflux ratio. Bottoms stream 32 is fed to tower 33, which recovers the propylene as stream 35. Tower 33 is operated at an overhead pressure of 200 psig and with a reflux ratio of 2:1 by weight. The overhead temperature is 87° F. and the bottoms temperature is 210° F. Finally, C$_4$ olefins are recovered as distillate from tower 37 as stream 38. The bottoms stream 39 from tower 37 contains mostly C$_5$+ hydrocarbons, which are useful as fuel. Tower 37 is operated at 100 psig and with a 3:1 recycle ratio by weight. It contains 30 ideal stages.

This example shows that high yields of valuable products (ethylene, propylene, and isoprene) can be produced from a raffinate-1 stream.

head stream in the presence of a first metathesis catalyst to generate a second reaction mixture comprising isoamylenes, butenes, and propylene; (c) distilling the second reaction mixture to isolate isoamylenes; and (d) dehydrogenating isoamylenes from step (c) to produce isoprene.

2. The process of claim 1 further comprising reacting the bottoms stream from step (a) with ethylene in the presence of a second metathesis catalyst to produce a third reaction mixture comprising ethylene, propylene, 1-butene, 2-butene, and C$_5$ and higher olefins; distilling the third reaction mixture into ethylene, propylene, a butenes stream, and a heavy stream comprising the C$_5$ and higher olefins.

3. The process of claim 2 further comprising recycling the separated ethylene to the metathesis reaction of the bottoms stream from step (a) and ethylene.

4. The process of claim 3 further comprising recycling the butenes stream to step (a).

5. The process of claim 1 wherein the feed stream comprises 2-butene.

6. The process of claim 1 wherein the feed stream is raffinate-1.

7. The process of claim 1 wherein the isomerization catalyst is a basic catalyst.

8. The process of claim 1 wherein the isomerization catalyst comprises magnesium oxide.

9. The process of claim 1 wherein the isomerization catalyst is a hydroisomerization catalyst.

TABLE 1

Flow Rates of Components in Various Streams (lb/h)*

| Stream | 2 | 38 | 16 | 6 | 7 | 10 | 12 | 14 | 17 | 20 | 29 | 32 | 35 | 34 | 39 | 25 |
|---|---|---|---|---|---|---|---|---|---|---|---|---|---|---|---|---|
| CO and CO$_2$ | | | | | | | | | | 242 | | | | | | |
| CH$_4$ | | | | | | | | | | 256 | | | | | | |
| C$_2$H$_4$ | | | | | | 5270 | 5270 | | | 377 | 3469 | 19 | 19 | | | 3053 |
| C$_3$H$_6$ | | | 293 | | | 28124 | 27831 | 293 | | 121 | 9735 | 9716 | 9716 | | | |
| c-B2 | 7528 | 1508 | 8264 | 24626 | 9208 | 8299 | 1 | 8298 | 34 | 34 | 1508 | 1508 | | 1508 | | |
| t-B2 | 15148 | 2010 | 11047 | 43336 | 2699 | 11067 | 3 | 11064 | 17 | 17 | 2010 | 2010 | | 2010 | | |
| B1 | 37136 | 986 | 5363 | 9116 | 5 | 5395 | 31 | 5364 | 1 | 256 | 986 | 986 | | 986 | | |
| i-C$_4$= | 40748 | 21 | 35383 | 76122 | 30 | 35646 | 258 | 35388 | 5 | 5 | 21 | 21 | | 21 | | |
| 2M2B | | | 1 | | | 23457 | | 23457 | 23456 | 14308 | 10 | 10 | | 10 | 10 | |
| 2M1B | | | 6 | | | 8268 | | 8268 | 8262 | 5040 | | | | | | |
| 3M1B | | | 48 | | | 1118 | | 1118 | 1070 | 653 | | | | | | |
| t-2P | | | | | | 3638 | | 3638 | 3638 | 2219 | 356 | 356 | | 356 | 356 | |
| c-2P | | | | | | 1704 | | 1704 | 1704 | 1039 | 165 | 165 | | 165 | 165 | |
| 1-P | | | | | | 875 | | 875 | 875 | 534 | 85 | 85 | | 85 | 85 | |
| t-1,3-PD | | | | | | | | | | 1000 | | | | | | |
| c-1,3-PD | | | | | | | | | | 795 | | | | | | |
| Isoprene | | | | | | | | | | 11764 | | | | | | |
| C$_6$= | | | | | | 19787 | | 19787 | 19787 | 19787 | 114 | 114 | | 114 | 114 | |
| C$_7$= | | | | | | 552 | | 552 | 552 | 552 | 5 | 5 | | 5 | 5 | |
| Total | 100560 | 4525 | 60405 | 153200 | 11942 | 153200 | 33394 | 119806 | 59401 | 58999 | 18464 | 14995 | 9735 | 5260 | 735 | 3053 |

*c-B2 = cis-2-butene, t-B2 = trans-2-butene, B1 = 1-butene, 2M2B = 2-methyl-2-butene, 2M1B = 2-methyl-1-butene, 3M1B = 3-methyl-1-butene, t-2P = trans-2-pentene, c-2P = cis-2-pentene, 1-P = 1-pentene, t-1,3-PD = trans-1,3-pentadiene, c-1,3-PD = cis-1,3-pentadiene, C$_6$= = hexenes, C$_7$= = heptanes.

We claim:

1. A process comprising: (a) reacting a feed stream comprising 1-butene and isobutene in the presence of an isomerization catalyst to generate a first reaction mixture, and concurrently distilling the first reaction mixture to produce an overhead stream comprising 2-butene and isobutene and a bottoms stream comprising 2-butene; (b) reacting the over- 10. The process of claim 1 wherein the hydroisomerization catalyst comprises Pd and alumina.

11. The process of claim 10 wherein the feed stream comprises hydrogen.

12. The process of claim 10 wherein the isomerization reaction is performed at a temperature in the range of from 100 to 250° F.

13. The process of claim 10 wherein the isomerization reaction is performed at a pressure in the range of from 50 to 250 psig.

14. The process of claim 1 wherein the dehydrogenation reaction is performed at a temperature in the range of from 700 to 1300° F.

15. The process of claim 1 wherein the first metathesis catalyst comprises a transition metal oxide comprising an element selected from the group consisting of cobalt, molybdenum, rhenium, tungsten, and mixtures thereof.

16. The process of claim 1 wherein the first metathesis catalyst comprises tungsten oxide and silica.

17. The process of claim 16 wherein the first metathesis catalyst further comprises magnesium oxide.

18. The process of claim 2 wherein the second metathesis comprises a transition metal oxide comprising an element selected from the group consisting of cobalt, molybdenum, rhenium, tungsten, and mixtures thereof.

19. The process of claim 2 wherein the second metathesis catalyst comprises tungsten oxide and silica.

20. The process of claim 19 wherein the second metathesis catalyst further comprises magnesium oxide.

* * * * *